United States Patent [19]
Reich

[11] Patent Number: 5,672,883
[45] Date of Patent: *Sep. 30, 1997

[54] CONTAINER AND METHOD FOR TRANSPORTING A SYRINGE CONTAINING RADIOACTIVE MATERIAL

[75] Inventor: Don E. Reich, Westlake Village, Calif.

[73] Assignee: Syncor International Corporation, Woodland Hills, Calif.

[ * ] Notice: The term of this patent shall not extend beyond the expiration date of Pat. No. 5,536,945.

[21] Appl. No.: 614,795

[22] Filed: Sep. 11, 1996

Related U.S. Application Data

[62] Division of Ser. No. 214,681, Mar. 16, 1994, Pat. No. 5,519,931.

[51] Int. Cl.$^6$ ........................................... G21F 5/00
[52] U.S. Cl. ...................... 250/507.1; 250/506.1; 206/365; 600/5
[58] Field of Search ........................... 250/507.1, 506.1; 206/365; 600/5

[56] References Cited

U.S. PATENT DOCUMENTS

| | | | |
|---|---|---|---|
| D. 208,080 | 7/1967 | Hamilton | D83/12 |
| D. 324,101 | 2/1992 | Reif et al. | D24/112 |
| D. 333,347 | 2/1993 | Kemp et al. | 224/131 |
| 2,682,352 | 6/1954 | Hawkins et al. | 220/48 |
| 2,812,231 | 11/1957 | Zar | 21/56 |
| 3,074,542 | 1/1963 | Myerson et al. | 206/43 |
| 3,101,841 | 8/1963 | Baldwin | 206/43 |
| 3,149,717 | 9/1964 | Castelli | 206/43 |
| 3,272,322 | 9/1966 | Ogle | 206/43 |
| 3,294,231 | 12/1966 | Vanderbeck | 206/63.2 |
| 3,329,146 | 7/1967 | Waldman, Jr. | 128/221 |
| 3,344,787 | 10/1967 | Maclean | 128/221 |
| 3,367,488 | 2/1968 | Hamilton | 206/63.2 |
| 3,531,644 | 9/1970 | Koster | 250/106 |
| 3,673,411 | 6/1972 | Glasser | 250/106 |
| 3,677,247 | 7/1972 | Brown | 128/221 |
| 3,882,315 | 5/1975 | Soldan | 250/506 |
| 3,971,955 | 7/1976 | Heyer et al. | 250/507 |
| 4,081,688 | 3/1978 | Fries | 250/506 |
| 4,106,622 | 8/1978 | Windischman | 206/365 |
| 4,113,090 | 9/1978 | Carstens | 206/365 |
| 4,357,541 | 11/1982 | Ernst | 250/507.1 |
| 4,781,697 | 11/1988 | Slaughter | 604/192 |
| 4,846,235 | 7/1989 | Handke | 141/31 R |
| 4,851,702 | 7/1989 | Perlman | 250/507.1 |
| 4,869,299 | 9/1989 | Handke | 141/1 |
| 4,892,525 | 1/1990 | Hermann, Jr. et al. | 604/263 |
| 4,917,263 | 4/1990 | Korb | 220/404 |
| 5,096,062 | 3/1992 | Burkardt et al. | 206/361 |
| 5,099,998 | 3/1992 | Curzon et al. | 206/514 |
| 5,145,063 | 9/1992 | Lee | 206/364 |
| 5,157,900 | 10/1992 | Kupsersmit | 53/444 |
| 5,205,408 | 4/1993 | Cobb | 206/364 |
| 5,245,117 | 9/1993 | Withers et al. | 588/244 |
| 5,277,312 | 1/1994 | Vumbaca | 206/366 |
| 5,303,836 | 4/1994 | Childress | 220/1.5 |
| 5,323,719 | 6/1994 | Withers et al. | 110/346 |
| 5,385,105 | 1/1995 | Wither, Jr. et al. | 110/346 |
| 5,417,326 | 5/1995 | Winer | 206/366 |
| 5,536,945 | 7/1996 | Reich | 250/507.1 |

Primary Examiner—Jack I. Berman
Attorney, Agent, or Firm—Sheppard, Mullin, Richter & Hampton LLP

[57] ABSTRACT

A method and apparatus for transporting syringes containing radioactive material. The apparatus includes a radiopharmaceutical pig having an inner chamber in which a sharps container can be secured. The sharps container has a housing and an attachable cap. The method includes assembling the radiopharmaceutical pig so that the chamber of the radiopharmaceutical pig contains the syringe in the sharps container housing. The radiopharmaceutical pig is disassembled, where upon the syringe is removed, discharged, and then replaced in the sharps container housing. The cap of the sharps container is affixed to the housing of the sharps container, thus enclosing the contaminated syringe therein. The radiopharmaceutical pig is assembled so that its chamber contains the sharps container and the syringe. The radiopharmaceutical pig is transported to a disposal area, where it is disassembled and the sharps container containing the syringe is placed in a particular disposal container.

6 Claims, 5 Drawing Sheets

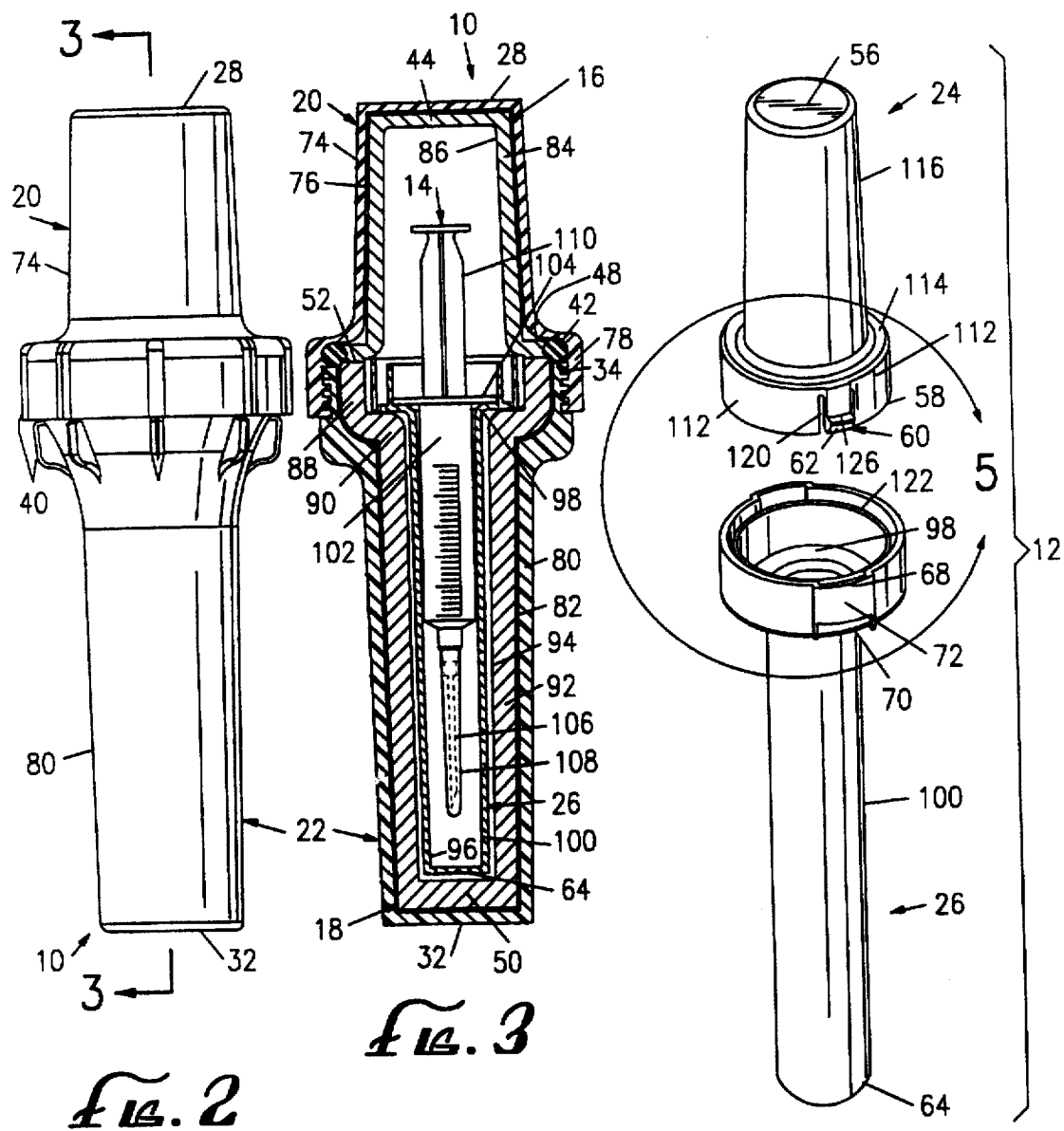

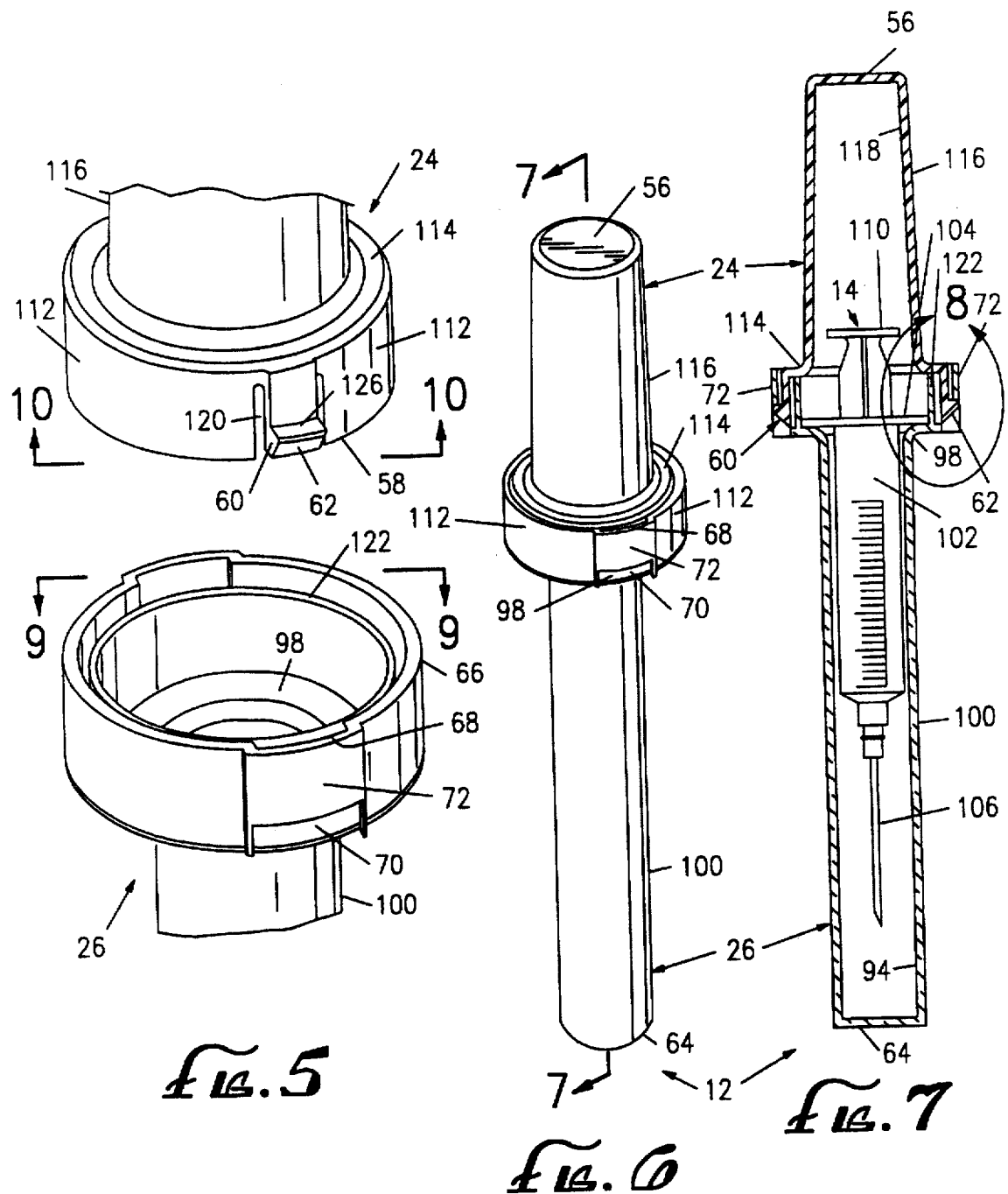

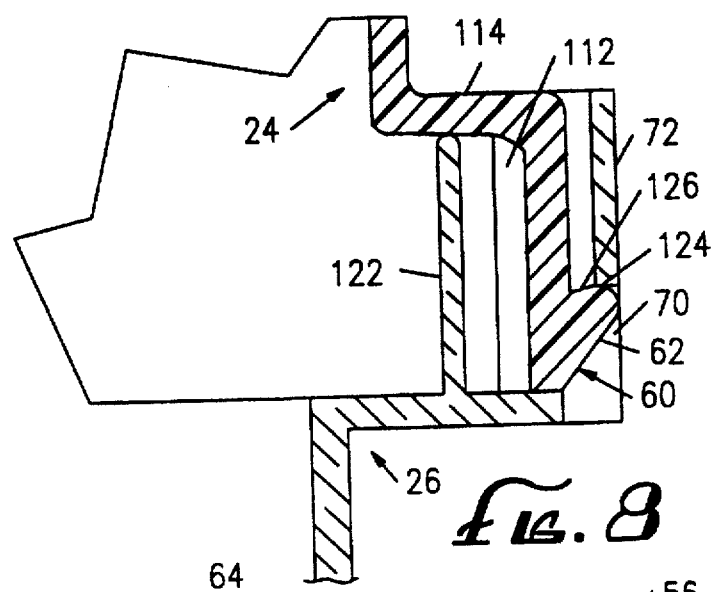
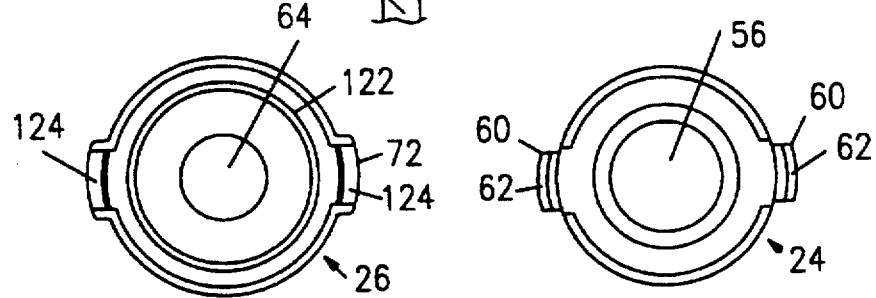
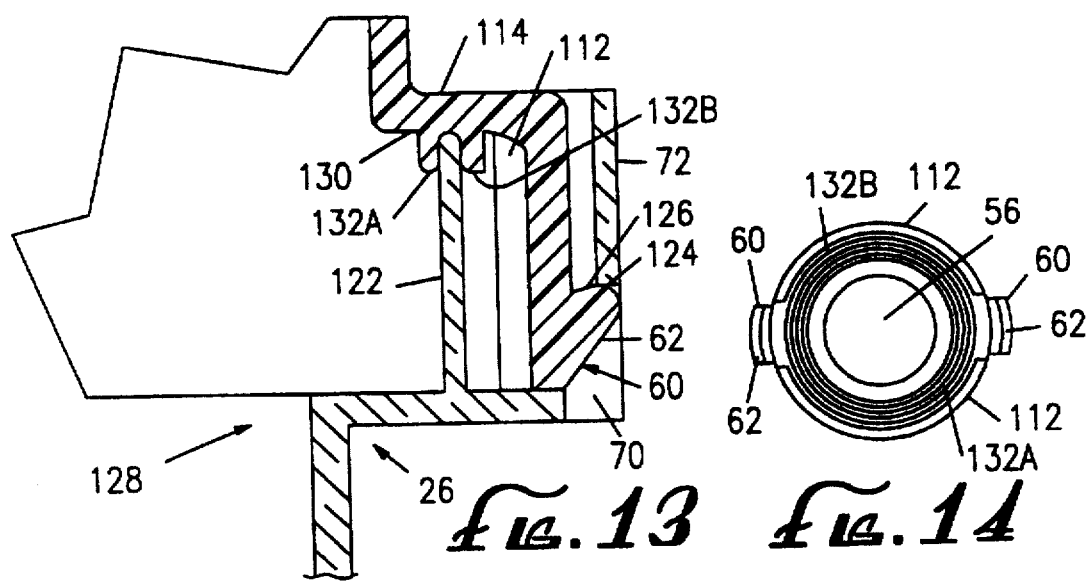

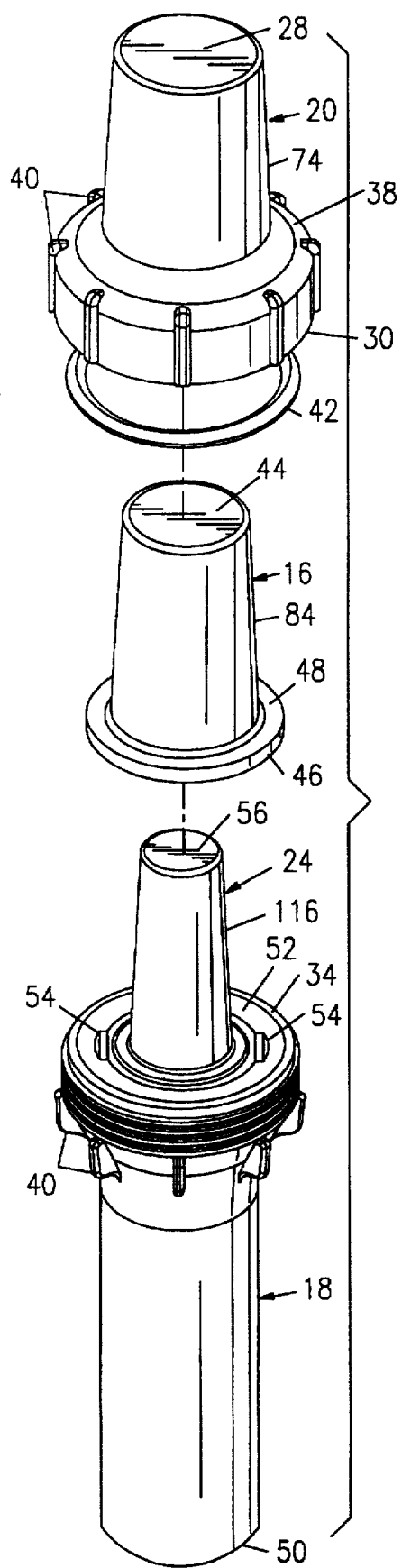
*fig.*11
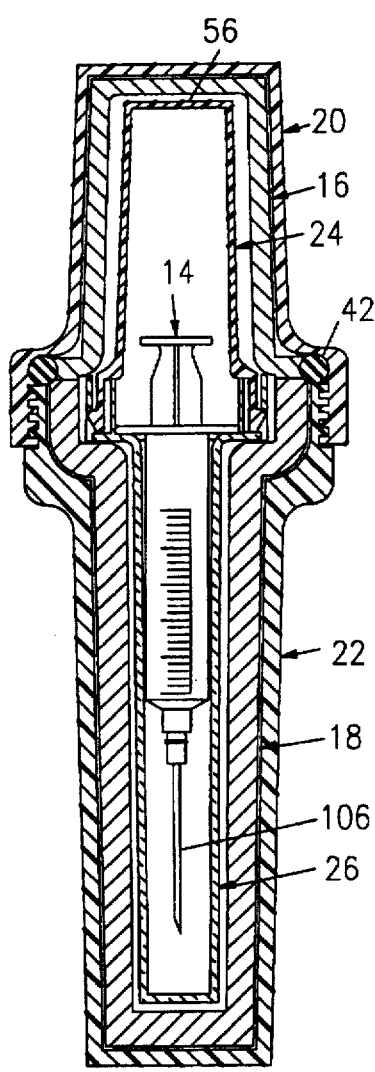
*fig.*12

CONTAINER AND METHOD FOR TRANSPORTING A SYRINGE CONTAINING RADIOACTIVE MATERIAL

This application is a division of application Ser. No. 08/214,681, filed Mar. 16, 1994, U.S. Pat. No. 5,519,931.

BACKGROUND OF THE INVENTION

The present invention relates to shielded containers for the transportation of radioactive sources and, more particularly, to the combination of a radiopharmaceutical pig with a sharps container capable of holding a syringe containing a radioactive drug.

In the medical industry, radioactive drugs are used for various applications, including the internal imaging of various human organs for diagnosis purposes. Over the years, the medical industry has developed many different radioactive drugs that are designed to concentrate around these human organs.

Generally, radioactive drugs are in a liquid form that is suitable for injection into a patient. Because of the radioactive characteristics of these drugs, they must be handled according to regulations promulgated by various departments of the United States government, including the Department of Transportation (DOT), the Nuclear Regulation Commission (NRC), and the Occupational Health and Safety Administration (OSHA). Accordingly, hospitals that make their own radioactive drugs must invest in the equipment and the training necessary to meet the requirements of such regulations.

Typically, a patient requires only a small dose of a specific radioactive drug. Therefore, depending on the number of patients, it is generally not economical for one hospital to maintain the staff and equipment to make the radioactive drugs required by that hospital's patients. Furthermore, the radioactive agents in the drugs have various half lives and lose their effectiveness after a predetermined time. Thus, if a hospital does not have the required demand, some of its unused radioactive agents may decay and become unusable. To avoid the expense of such in-house production of radioactive drugs, many hospitals now purchase each prescribed dose of a radioactive drug from an outside pharmacy.

The pharmacies which provide radioactive drugs to hospitals utilize the principles of mass production to reduce their per-unit costs. The pharmacies receive prescription orders and deliver the corresponding radioactive drugs to nearby hospitals. Each prescription is individually filled, and each dose of radioactive drug is packaged in a syringe intended for a specific patient. The syringes containing the radioactive drugs must be carefully handled and delivered inside containers offering some degree of radiation shielding. Furthermore, government regulations require syringes to be disposed of in a container that shields others from the risk of injury posed by their sharp hypodermic needles. Such a container, generally referred to as a "sharps" container, typically has an inner cavity or chamber that can hold syringes. One type of sharps container has a chamber sealed by a spring biased pivoting gate to keep syringes safely inside.

One type of delivery container currently used for the delivery of syringes containing radioactive drugs is known as a radiopharmaceutical pig. The radiopharmaceutical pig typically is a two-part assembly and has an inner chamber suitable for carrying a syringe. The chamber is lined with a radiation shielding material, typically elemental lead. The exterior of the radiopharmaceutical pig is generally a plastic polystyrene shell. The polystyrene shell on one part of the radiopharmaceutical pig has elongated ridges projecting radially from the periphery of its external surface. If the assembled radiopharmaceutical pig is laid on its side, these ridges prevent it from accidentally rolling in an uncontrolled manner.

The identity of the radioactive drug within the syringe must be identified for proper use and disposal. To facilitate efficient disposal, syringes containing residuals of radioactive drugs with similar half lives are placed in the same disposal containers. To identify the radioactive drug within the syringe, labels typically are placed on the outside of the radiopharmaceutical pig and on the syringe within.

A common method for delivering the radioactive syringe is well known and includes the placement of the syringe with the required dose of a radioactive drug into the chamber of the radiopharmaceutical pig. The radiopharmaceutical pig is then delivered to the hospital where it is disassembled and the syringe is used according to other, well known, safety standards.

After the dose is injected into the patient, the syringe is referred to as "spent," but generally contains a small amount of residual radioactive drug. In addition to the radioactive contamination, the hypodermic needle of the spent syringe is biologically contaminated from contact with the patient. In view of the threat from such contamination, the pharmacy may also offer services for the disposal of the spent syringe. Accordingly, the spent syringe can be sent back to the pharmacy for proper disposal.

If the pharmacy offers disposal services, the spent syringe may be placed back into the radiopharmaceutical pig for a return trip to the pharmacy. Once the radiopharmaceutical pig arrives at the pharmacy, an employee manually removes the syringe from the chamber of the radiopharmaceutical pig by manually opening the radiopharmaceutical pig and dumping the exposed, contaminated syringe into a suitable disposal container.

While the previously discussed apparatus and method for delivering and disposing of syringes containing radioactive drugs is generally effective, under certain conditions there may be drawbacks associated with the devices and methods designed according to the prior art. One such drawback is the additional expense arising from contamination of the radiopharmaceutical pig. During the return trip to the pharmacy, the residual radioactive drug and biological contaminants in the syringe may leak and contaminate the inside chamber of the radiopharmaceutical pig. If such contamination occurs, government regulations require that the radiopharmaceutical pig must be emptied by non-manual means (i.e., by robotic arms or their equivalent), and then disinfected with the appropriate chemicals. Such a process is expensive and, therefore, undesirable.

Another drawback is the danger of biological contamination posed by the sharp hypodermic needle of the spent syringe. As discussed above, methods and apparatus of the prior art allow the contaminated needle to become exposed during the pharmacy's disposal operations. However, under current U.S. government regulations, a spent syringe needs to be disposed of within a sharps container. Generally, if a spent syringe is not within such a protective sharps container, further handling of the syringe raises safety and regulatory concerns. Such safety concerns necessitate additional safety procedures and handling equipment that can be undesirably expensive. For example, a hospital may dispose of the syringe in sharps containers on the hospital premises. However, such a disposal system necessitates the expense of monitoring and tracking the syringes because of their radioactivity.

Yet another drawback is the lack of roll-resistance of the disassembled radiopharmaceutical pigs designed according to the prior art. As described previously, only one part of the radiopharmaceutical pig has roll-resistant ridges.

Accordingly, the radiopharmaceutical pig is roll-resistant only when its two parts are secured together. Because the remaining part itself has no ridges, when the radiopharmaceutical pig is disassembled, the part without ridges may move in an uncontrolled manner causing accidental contamination or injury.

Still another drawback is associated with the durability of the polystyrene shell on the exterior of the radiopharmaceutical pig. The polystyrene shell is relatively brittle and may break or chip upon impact with other objects. If the polystyrene shell breaks, the inner liner of elemental lead can become dislodged, which may lead to the escape of dangerous radiation from the chamber of the radiopharmaceutical pig. Furthermore, if the two parts of the radiopharmaceutical pig are secured together by a threaded portion on the polystyrene shell, cracking of the shell may necessitate replacement of the entire radiopharmaceutical pig.

Accordingly, there exists a need for a method and apparatus for transporting a syringe containing radioactive material that safely encloses the spent syringe and reduces the possibility of contamination of the radiopharmaceutical pig. Still another need exists for a radiopharmaceutical pig that has a durable shell and is roll-resistant when in an unassembled condition.

SUMMARY OF THE INVENTION

The present invention resides in an improved method and apparatus for transporting a syringe containing radioactive material that provides for the safe enclosure of the spent syringe and reduces the possibility of contamination of the radiopharmaceutical pig. The present invention also provides a radiopharmaceutical pig that has a durable shell and is roll-resistant when in an unassembled condition.

The present invention includes a method for transporting a syringe containing radioactive material to a location for use and, thereafter, to a disposal area. The method begins with the insertion of a housing into a lower portion of a radiopharmaceutical pig. The syringe is then inserted into the housing. Next, the radiopharmaceutical pig is assembled by securing an upper portion to the lower portion so that the radiopharmaceutical pig contains the syringe and the housing in an inner chamber. After the radiopharmaceutical pig is assembled, it is transported to the location for use. At the location, the radiopharmaceutical pig is disassembled by removing the upper portion from the lower portion. When the radiopharmaceutical pig is disassembled, the inner chamber is accessible for removal of the syringe from the housing.

After the syringe is removed from the housing, to allow for the discharge of at least some of the radioactive material from the syringe, the syringe is then replaced in the housing, which preferably has remained in the lower portion of the pig. A cap is attached to the housing to form a sharps container that contains the syringe therein. After the cap is attached to the housing, the radiopharmaceutical pig is reassembled by securing its upper portion to its lower portion. When the radiopharmaceutical pig is reassembled, the cap and the housing contain the syringe.

The radiopharmaceutical pig is then transported from the location of use to the disposal area. At the disposal area, the radiopharmaceutical pig is disassembled by removing the upper portion from the lower portion to expose the cap and the housing containing the syringe. The cap and the housing, containing the syringe, are then removed from the radiopharmaceutical pig and disposed of. Because the syringe is contained within the housing and the cap, it is not exposed to persons at the disposal area. Accordingly, such persons are advantageously protected from a sharp, contaminated needle on the syringe. Furthermore, because the cap and the housing contain the contaminated syringe, the radiopharmaceutical pig is less likely to become contaminated. The avoidance of such contamination provides a cost savings because an expensive decontamination procedure is avoided.

In a more detailed feature of the invention, a label is affixed to the syringe before the syringe is placed in the housing. The label contains information regarding the radioactive material within the syringe.

In another more detailed feature of the invention, the disposal of the cap and housing containing the syringe includes the reading of the information on the syringe label while the syringe is inside the cap and housing. The information is used to determine a particular disposal container for the syringe. The cap and housing, containing the syringe, are then placed into that particular disposal container. While in the disposal area, the particular disposal container can be determined without separating the cap from the housing. Thus, the employees are advantageously protected from the sharp, contaminated needle on the syringe.

In another more detailed feature of the invention, the uncontrolled rolling of the radiopharmaceutical pig is prevented by roll-resistant ridges on both the upper and the lower portions of the radiopharmaceutical pig. The ridges extend radially from the external circumference of the upper portion and from the external circumference of the lower portion. Because the lower portion also has roll-resistant ridges, that portion of the radiopharmaceutical pig is less likely to roll uncontrollably, thereby reducing the likelihood of injury or damage from an accident.

In a separate and independent feature of the invention, another method which covers the steps which may be completed by an outside pharmacy. Generally, an outside pharmacy will not use the syringe or handle the radiopharmaceutical pig while it is at the location of use.

Accordingly, the method covers the same general steps as discussed above but does not include those steps which the pharmacy will not regularly provide, such as: the disassembly of the radiopharmaceutical pig; the removal and use of the syringe; the replacement of the syringe into the housing; the attachment of a cap onto the housing, thereby containing the syringe therein; and the reassembly of the radiopharmaceutical pig.

In a separate and independent feature of the invention, a method provides for steps which may be completed by the healthcare staff. The method utilizes a radiopharmaceutical pig and a container having a housing and a cap. The container is configured to fit within a chamber in the radiopharmaceutical pig. The method begins with the disassembly of the radiopharmaceutical pig by the removal of an upper portion of the radiopharmaceutical pig from a lower portion of the radiopharmaceutical pig. The syringe is exposed when the radiopharmaceutical pig is disassembled. The exposed syringe is then removed from the housing and discharged. The discharging of the syringe removes at least some of the radioactive material from the syringe. The syringe is then replaced in the housing and a cap is attached to the housing so that the syringe is inside the container. Finally, the radiopharmaceutical pig is assembled by securing the upper portion to the lower portion so that the radiopharmaceutical pig contains the container with the syringe inside.

The present invention also provides for an improved transportation container for a syringe containing radioactive material. The container includes a radiopharmaceutical pig having an internal chamber adapted to a cap and a housing forming a sharps container. The cap has at least one resilient snap that engages at least one ledge on the housing to safely contain the syringe within the sharps container. This transportation container allows the contaminated syringe to be transported to the disposal area, where it can be handled, thereby saving the hospital the in-house disposal costs associated with known sharps containers.

In a more detailed feature of the invention, the transportation container includes a radiopharmaceutical pig having an outer shell made of relatively stronger ABS plastic. Another more detailed feature of the invention, the housing is transparent, thereby advantageously enabling the user to view a contaminated syringe without risk.

Other features and advantages of the present invention will become apparent from the following description of the preferred embodiment, taken in conjunction with the accompanying drawings, which illustrate, by way of example, the principles of the invention.

BRIEF DESCRIPTION OF THE DRAWINGS

The following drawings illustrate the invention. In such drawings:

FIG. 2 is an elevational view showing the assembled radiopharmaceutical pig;

FIG. 3 is a cross sectional elevational view showing a syringe resting in the housing of the sharps container within the chamber of the radiopharmaceutical pig shown in FIG. 2;

FIG. 4 is an exploded perspective view of the sharps container shown in FIG. 1;

FIG. 5 is a perspective view of the mating ends of the sharps container, taken about line 5 in FIG. 4;

FIG. 6 is a perspective view of the assembled sharps container, showing the cap of the sharps container attached to the housing of the sharps container, according to the first embodiment of the invention;

FIG. 7 is a cross-sectional elevational view of the syringe within the sharps container shown in FIG. 6;

FIG. 8 is a partial cross sectional view of the assembled sharps container taken about line 8 in FIG. 7;

FIG. 9 is a top view of the sharps container housing showing in FIG. 5;

FIG. 10 is a bottom view of the sharps container cap shown in FIG. 5;

FIG. 11 is an exploded perspective view showing the sharps container within the partially assembled radiopharmaceutical pig of FIG. 1;

FIG. 12 is a cross sectional elevational view of the assembled sharps container within the radiopharmaceutical pig according to the first embodiment of the invention;

FIG. 13 is a partial cross sectional view of the assembled sharps container according to the second embodiment of the invention;

FIG. 14 is a bottom view of the sharps container cap shown in FIG. 13.

DESCRIPTION OF THE PREFERRED EMBODIMENT

Figure 1:
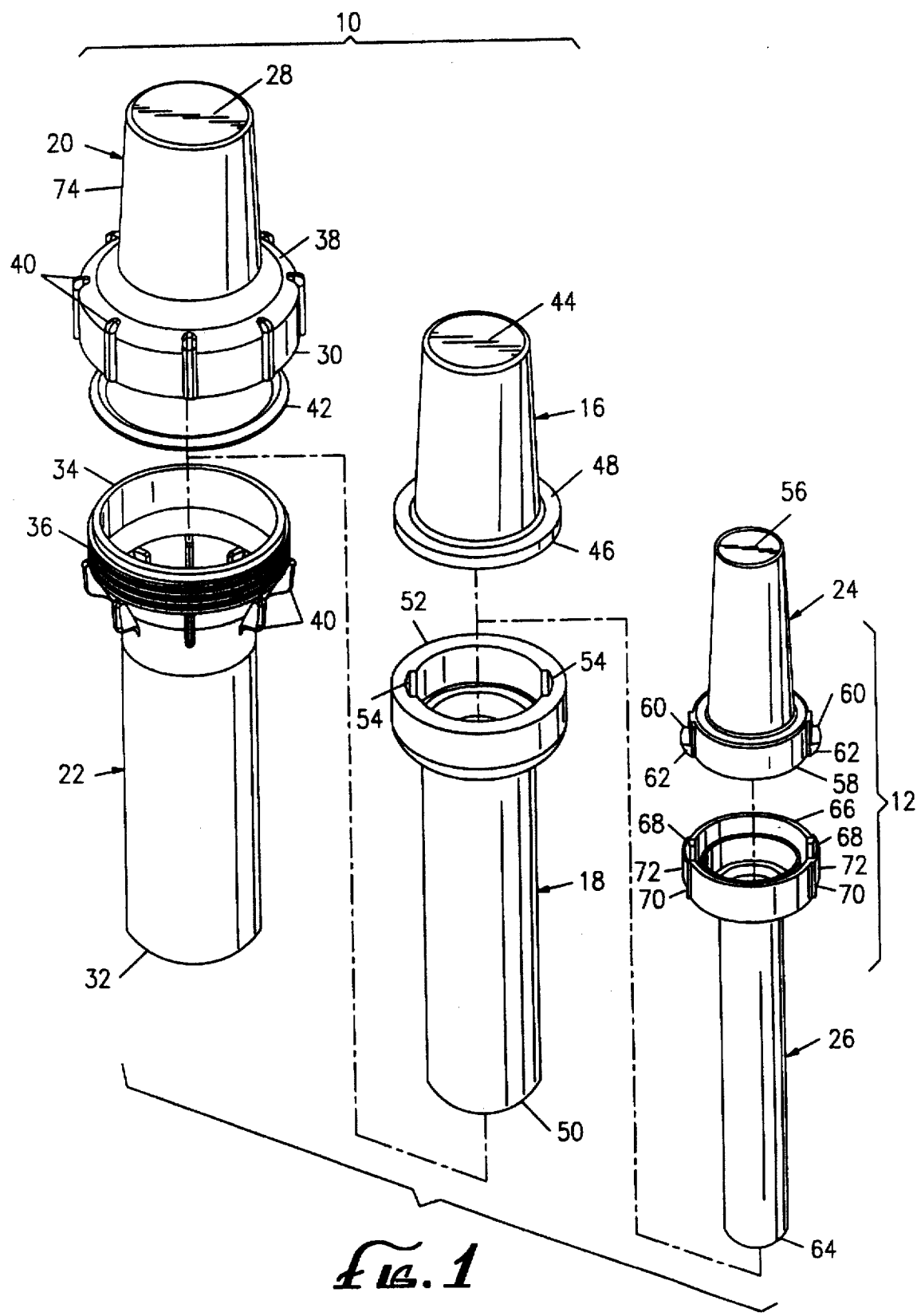
FIG. 1 is a perspective view of an exploded radiopharmaceutical pig and sharps container, showing the relative placement of the sharps container within the components of the radiopharmaceutical pig.

As shown in the exemplary drawings, the present invention comprises a radiopharmaceutical pig 10 and a sharps container 12 for a syringe 14 holding a radioactive drug. The syringe holding the radioactive drug fits within the sharps container, which, in turn, fits within the radiopharmaceutical pig. The sharps container meets U.S. government regulations, such as 29 C.F.R. §1910.1030, for protective containers that house materials having biologically contaminated, sharp edges.

FIGS. 1 and 11 show the interrelationship between the components of the radiopharmaceutical pig 10 and the sharps container 12. The structural components of the radiopharmaceutical pig include an upper shield 16 and a lower shield 18 than nest within an upper outer shell 20 and a lower outer shell 22, respectively. The sharps container has an upper cap 24 and a lower housing 26 that nest within the upper shield and the lower shield, respectively.

The upper shell 20 of the radiopharmaceutical pig 10 has a generally tubular, cup-like shape. The upper shell has a closed end 28 and an open mating end 30 with internal threads (not shown in FIG. 1 or 11). Similarly, the lower shell 22 has a generally tubular, elongated cup-like shape featuring a closed end 32 and an open mating end 34 with external threads 36. The mating end of the upper shell has a flange 38 to provide for the internal threads that engage the external threads located on the mating end of the lower shell. Both shells have interior surfaces sized to accept their respective shields 16 and 18.

External anti-roll ridges 40 are circumferentially located adjacent to the mating ends 30 and 34 of the upper 20 and the lower 22 shells. If the lower shell is placed on its side, these ridges advantageously tend to prevent it from rolling, or otherwise moving, in an uncontrolled manner. Due to the weight of the shields 16 and 18 within each shell, uncontrolled rolling of either shell may damage the pig itself or injure an attending worker. Further, if the lower shell is not secured to the upper shell, the syringe 14 may dislodge from within the lower shield and fracture or poke attending workers. Therefore, unlike the prior art discussed above, the anti-roll ridges are also placed on the lower shell so as to prevent the rolling of the lower shell when it is not connected to the upper shell. Accordingly, the risk of injury from a dislodged syringe or damage to the radiopharmaceutical pig is advantageously minimized.

The upper 20 and lower 22 shells are preferably constructed from an ABS plastic, such as ABS Sinkral B-54 acrylonitrile butadine styrene from Enichem America, Inc., 1211 Avenue of the Americas, New York, N.Y. 11436. ABS plastic material is more durable than the polyethylene plastic utilized by the radiopharmaceutical pigs made according to the prior art. Accordingly, each shell is less likely to crack or fracture. Therefore, the preferred radiopharmaceutical pig 10 has a longer useful life, thereby advantageously reducing expenses by minimizing the need for replacement of broken radiopharmaceutical pigs. The upper and lower shells also may be constructed of any other material suitable for a given application.

An "O" ring 42 fits between the upper shell 20 and the lower shell 22 to provide an air and fluid tight seal. The "O" ring is preferably made from a nitrile rubber, such as Nitrile from DWA Industrial Products, Inc., 9780 Variel Avenue, Chatsworth, Calif. 91311. However, the "O" ring could be made from any other material suitable for providing an effective seal.

The other components of the radiopharmaceutical pig 10 are the upper shield 16 and the lower shield 18. The upper shield has a generally tubular, cup-like shape featuring a closed end 44 and an open end 46 with a circumferential flange 48. The lower shield has a generally tubular, elongated cup-like shape featuring a closed end 50 and an open mating end 52. Both shields have internal chambers or cavities sized to accept the sharps container 12.

The external dimensions of the upper 16 and lower 18 shields are sized so that the upper and lower shields nest within the upper 20 and lower 22 shells, respectively. The circumferential flange 48 on the mating end 46 of the upper shield abuts the mating end 52 of the lower shield when the radiopharmaceutical pig 10 is assembled. The mating end of the lower shield has preferably two opposed internal side cutouts 54 sized to accept the notches 68 in the housing 26 of the sharps container 12 as discussed below. The upper and lower shields are preferably constructed of elemental lead, but may be constructed of any material that inhibits the passage of radiation. The upper and lower shields also can be constructed from a thermoplastic polycarbonate condensation product of bisphenol-A and phosgene, sold under the trademark Lexan by the General Electric Company, Polymers Products Department, Pittsfield, Mass. 01201. In a suitable thickness, the Lexan material blocks certain types of radiation to an acceptable extent as is known in the art. Furthermore, according to well known principles, the shields also can be constructed of depleted uranium, tungsten, Plexiglass® or other materials suitable for the radiation associated with a given application.

The sharps container 12 has a hollow tubular, cup-shaped cap 24 and a long, hollow tubular housing 26. The external dimensions of the cap and the housing are sized so that the cap and the housing preferably nest within the upper 16 and lower 18 shields, respectively.

The cap has a closed end 56 and an open mating end 58 with preferably two resilient snaps 60. Each snap has an externally bevelled face 62. The cap of the sharps container 12 is preferably made from a red-colored polypropylene material, such as polypropylene PP Hival 2420 from Ashland Chemical, Inc., P.O. Box 2219, Columbus, Ohio 43216. U.S. government regulations, e.q., 29 C.F.R. §1910.1030, require that a sharps container be labeled appropriately, and one means of satisfying such regulations is by coloring the closure red, which signifies that the sharps container contains regulated medical waste. Further means of satisfying such regulations is by labeling the sharps container with the word "biohazard" or the well known international biohazard symbol.

The long, hollow tubular housing 26 is preferably made from a transparent polystyrene material, such as Styron® 666D clear polystyrene from Dow U.S.A., Dow Chemical, Midland, Mich. 48764. Because the material is transparent, the interior of the housing can be viewed without disassembly of the sharps container 12. The entire housing need not be transparent; rather, the housing may be made from an opaque material having a small, transparent window that provides a view of the interior. The housing also need not be constructed of a transparent material if the contents of the sharps container can be ascertained by other means, such as by the appropriate labelling of the exterior of the sharps container. The housing and the cap 24 may also be constructed from other materials of suitable strength. It should be noted that the drawings do not show the structure behind the transparent surfaces of the housing solely to avoid confusion from the additional lines that would be required.

The housing has a closed end 64 and an open mating end 66 with two opposed notches 68 sized to engage the resilient snaps 60 on the cap 24. Each notch is positioned longitudinally above a rectangular side opening 70 sized to accept the resilient snaps. The diametrical distance across the opposed notches is greater than the diametric distance between the lower edges of the beveled faces on the snaps but less than the diametric distance across the upper edges of the beveled faces on the snaps. Accordingly, the resilient snaps deflect radially inward as the cap passes through the notches leading to the rectangular side openings formed in the housing. The diametrical distance between the external surfaces 72 of each notch is less than the diametric distance between the cutouts 54 on the lower shield 18. Accordingly, the notches fit within the cutouts on the lower shield. Because the notches of the housing fit within the cutouts of the lower shield, the housing will not rotate when it is nested in the lower shield.

FIGS. 2 and 3 depict the front and cross-sectional views of an assembled radiopharmaceutical pig 10 containing the syringe 14 resting within the housing 26 of the sharps container 12. The upper shell 20 and the lower shell 22 are threadably engaged and sealed by the "O" ring 42. The upper shell preferably has a tapered side wall 74 that defines an inner cavity 76 extending from its internal threads 78 to its closed end 28. The "O" ring is located longitudinally between the side wall of the upper shell and the mating end 34 of the lower shell. Thus, the "O" ring advantageously prevents radioactive material from escaping the space within the mated upper and lower shields. The lower shell has a tapered side wall 80 that defines an inner cavity 82 extending from its mating end 34 to its closed end 32.

The upper shield 20 also preferably has a tapered side wall 84 than defines an inner cavity 86 extending from its flange 48 to its closed end 44. The lower shield 22 has a generally cylindrical wall 88 on its mating end 52. The cylindrical wall abuts a shoulder 90 that extends radially inward to a smaller diameter, preferably tapered side wall 92. The tapered side wall defines an inner cavity 94 extending to the closed end 50 of the lower shield.

Both the upper 16 and lower 18 shields are preferably permanently affixed to the upper 20 and lower 22 shells by a glue or an adhesive, such as APC 324E Two Part Epoxy Resin from Advanced Polymer Concepts, Inc., W1102 N11774 Maple Road, Germantown, Wis. 53022. However, other well known fastening methods such as welding or mechanical fastening may be used.

In the preferred embodiment of the invention, the lower portion of the radiopharmaceutical pig 10 comprises the lower shell 22 permanently affixed to the lower shield 18. Similarly, the upper portion of the preferred radiopharmaceutical pig includes the upper shell 20 permanently affixed to the upper shield 16. However, it should be understood that the scope of the invention encompasses a radiopharmaceutical pig having shields that are not fastened to the shells. Furthermore, in the claims, the term "lower portion of the radiopharmaceutical pig" is intended to include a lower shield alone or combined with a lower shell. Similarly, the term "upper portion of the radiopharmaceutical pig" is intended to include an upper shield alone or combined with an upper shell.

The housing 26 of the sharps container 12 nests within the cavity 94 of the lower shield 18. A shoulder 98 extends radially inward from the mating end of the housing to a tapered side wall 100. The side wall defines an inner cavity 96 extending to the closed end 64 of the housing.

The syringe 14 has a generally tubular body 102 with a flanged base 104, a hypodermic needle 106, a cap 108, and a plunger 110. The body and needle of the syringe nest within the inner cavity 96 of the housing 26. The plunger fits within the inner cavity 86 of the upper shield 16. The word "syringe" as used herein means any container housing material having sharp edges that could become biologically contaminated, thereby requiring disposal within a protective container mandated by government regulations. In this regard, is to be understood that the present invention is not to be limited by the size, shape, or function of the syringe itself.

FIGS. 4 and 5 depict exploded perspective views of the cap 24 and the housing 26 of the sharps container 12. The mating end 58 of the cap has two partially cylindrical walls 112 between the two resilient snaps 60. The partially cylindrical walls and the snaps extend from a generally horizontal shoulder 114. The shoulder extends radially inward to a tapered side wall 116 that defines a cavity 118 extending to the closed end 56 of the cap. The resilient snaps 60 are separated from the partially cylindrical walls by cutouts 120 that preferably extend to the shoulder of the cap. The snaps have an inside diameter slightly larger that the inside diameter of the partially cylindrical walls. The length of the cutouts varies with the characteristics of the material from which the cap is constructed, but approximately ⅜ is generally acceptable for a cap constructed of the preferred polypropylene material.

FIGS. 6 and 7 show the assembled sharps container 12 with the syringe 14 sealed inside. Note that the syringe does not have a cap over its hypodermic needle 106. However, the sharps container also may contain a syringe having a cap over its hypodermic needle. The inner cavity 118 of the cap 24 houses the extended plunger 110 of the syringe.

The shoulder 98 of the sharps container housing 26 is sized to support the flanged base 104 of the syringe body 102, thereby supporting the syringe 14 so that its needle 106 and body are within the cavity 96 project toward the closed end 64 of the housing. Because the flanged base of the syringe rests on the shoulder of the housing, the syringe is easily inserted with the needle pointing toward the closed end of the housing. Therefore, the fit between the shoulder of the housing and the flanged base of the syringe facilitates placement of the syringe into a position where the needle is immediately shielded within the housing. If the syringe is placed into the housing with its needle pointing upward, the needle poses a threat to persons trying to affix the cap 24 to the housing. Such persons are discouraged from such placement of the syringe because the syringe does not easily rest on the shoulder of the housing when it is in such a reversed position. Furthermore, the sharps container 12 cannot be closed with the syringe pointing upward because the inner cavity 118 of the cap preferably is not long enough to accommodate the body 102 and the needle of the syringe. Accordingly, the sharps container is advantageously configured to encourage the placement of the syringe with its needle safely protected within the housing.

The cap 24 and the housing 26 of the sharps container 12 form a seal capable of resisting leakage of the radioactive drug, blood, or other contaminates from within the sharps container. As shown in FIGS. 8, 9, and 10, a cylindrical sealing wall 122 extends longitudinally from the shoulder 98 of the housing toward the open mating end 66 of the housing. The sealing wall abuts the shoulder 114 of the sharps container cap, thereby forming a leak resistant seal.

As discussed above, the resilient snaps 60 on the cap 24 are sized to fit within the rectangular openings 70 in the housing. Each rectangular opening has a generally horizontal upper ledge 124. Each snap has an upper ridge 126 sized to abut the ledge of the rectangular opening so that the sharps container 12 cannot be disassembled by merely pulling the cap apart from the housing 26. Of course, if enough force or other tampering is applied to the sharps container 12, the cap will separate from the housing.

An alternative embodiment shown in FIGS. 13 and 14 depicts a sharps container 128 having a different leak resistant seal. In this embodiment, the inner surface 130 of the shoulder 114 of the cap 24 has concentric ridges 132a and 132b that are spaced apart to accept the sealing wall 122 of the housing 26. Such a configuration also provides a leak resistant seal.

Together, the radiopharmaceutical pig 10 and the sharps container 12 can be used to transport and dispose of the syringe 14 without the contamination dangers posed by known radiopharmaceutical pigs. When a patient needs a dose of a radioactive drug, a heathcare official, such as a doctor or nurse, transmits a prescription to a pharmacy, where the drugs are packaged in syringes 14 using well known medical practices. A label containing information regarding the drug is preferably affixed to the body 102 of the syringe. The following information may be included on the label: the patient's name, the production lot number, the expiration date of the drug, the quantity of the drug, the name of the intended medical procedure, and possibly other relevant information, such as a relevant order number or the drug's radioactive half life. A larger label with similar information is also preferably affixed to the radiopharmaceutical pig.

In this regard, the labels for the syringe 14 and the radiopharmaceutical pig 10 can contain any suitable information, such as words, bar code, or color code. It should be understood that the invention is not limited by the method of encoding and decoding the information contained on the labels, nor by the actual content of the information on the labels.

Once the radioactive drug is packaged within the syringe 14 at the pharmacy, the sharps container housing 26 is placed within the inner cavity 94 of the lower shield, which is part of the lower portion of the radiopharmaceutical pig 10. The syringe is then placed into the inner cavity 96 of the sharps container housing so that its capped needle 106 projects toward the closed end 64 of the housing. As shown in FIG. 7, the plunger 110 may protrude from the housing. The cap 24 of the sharps container 12 preferably is not attached to the housing at this time to make the syringe easily accessible at the hospital. Accordingly, the hospital preferably has a pre-ordered supply of caps. In other embodiments of the invention, the cap could be placed loosely above the housing so that the syringe can be easily removed from the radiopharmaceutical pig by a hospital employee. Alternatively, if the cap is easily removable from the housing, the cap may be attached to the housing at the pharmacy.

Next the upper portion of the radiopharmaceutical pig 10 is positioned above the lower portion of the radiopharmaceutical pig so that the mating ends 46 and 52 of the upper 16 and lower 18 shields are in opposed alignment. The upper portion of the radiopharmaceutical pig is then lowered onto the lower portion of the radiopharmaceutical pig and rotated until the threads 78 of the upper shell 20 tightly engage the threads 36 of the lower shell 22. As shown in FIG. 3, the now assembled radiopharmaceutical pig contains the sharps container housing 26 and the syringe 14 containing the radioactive drug.

Once the upper portion and the lower portion of the radiopharmaceutical pig 10 have been joined, the radiopharmaceutical pig is placed in a shipping container (not shown) meeting government regulations for the transportation of radioactive substances. Typically, this shipping container has a bottom foam rubber pad with many circular holes, each shaped to accept the lower shell of a radiopharmaceutical pig, and a top rubber pad with similar holes to accept the upper shells of radiopharmaceutical pigs. Alternatively, the holes within the rubber pads can be shaped to hold a radiopharmaceutical pig laying on its side. Shipping containers for shipping radiopharmaceutical pigs are well known and may have the general design of a metal briefcase-type container or a metal box commonly referred to as an "ammo can."

The shipping container is preferably transported to the destination via motor vehicle, aircraft, or hand delivery. When the syringe 14 is needed the radiopharmaceutical pig 10 is remvoed from the shipping container and placed on a laboratory table or the like. The upper portion of the radiopharmaceutical pig is then rotated and removed, thereby exposing the syringe. Using well known safety procedures, the syringe is removed by, e.g., a doctor or nurse, who injects the patient, thereby discharging the radioactive drug from the syringe. After the injection, the syringe may be biologically contaminated and generally contains a small amount of residual radioactive drug.

After the injection, the spent syringe 14 is reinserted into the inner cavity 96 of the housing 26 of the sharps container 12, which preferably is still resting within the lower portion of the radiopharmaceutical pig 10. A sharps container cap 24 is then placed so that its mating end 58 is in opposed alignment with the mating end 66 of the housing 26. The sharps container cap is placed over the plunger 26 of the syringe and moved towards mating end 66 of the housing until the resilient snaps 60 nearly contact the mating end of the housing. The cap is then rotated, if necessary, so that the resilient snaps are aligned with the notches 68 in in the housing, at which point the cap is forced downward, thereby causing the beveled faces 106 of the resilient snaps to engage the notches. As a result of the contact with the notches, the resilient snaps deflect radially inward and pass downward toward the rectangular openings 70. When the resilient snaps reach the openings, the resiliency of the preferred polypropylene material causes the snaps to assume their original position and lock the cap to the housing. The upper ridge 126 of each snap abuts the ledge 124 of its associated rectangular opening, thereby preventing the separation of the cap from the housing by the application of a longitudinal tensile force.

Once the spent syringe 14 is safely contained within the sharps container 12, the radiopharmaceutical pig 10 is assembled by threadably engaging the upper and lower portions so that the sharps container is enclosed inside the cavities 86 and 94 of the upper and lower shields 16 and 18. The assembled radiopharmaceutical pig is placed in an "ammo can" type shipping container for transport to the disposal area, which may be at the pharmacy. The shipping container is transported to the disposal area, preferably by a motor vehicle, while the radiopharmaceutical pig is disassembled by threadably removing the upper portion from the lower portion. When the upper portion of the radiopharmaceutical pig has been removed, the cap 24 of the sharps container is exposed because it extends upward from the lower portion of the radiopharmaceutical pig. The sharps container is then removed, which allows the label on the syringe 14 to be read through the transparent housing 26. The information on the label enables the determination to be made of the proper disposal container for the syringe within the sharps container. The sharps container, with the spent syringe inside, is disposed of by placing it in the particular disposal container for radioactive material having the half-life of the radioactive residual.

A primary advantage of the apparatus and method of this invention is the receipt of the spent syringe 14 within the sharps container 12 at the disposal area, which satisfies U.S. government regulations for the handling of biologically contaminated syringes. Upon opening the radiopharmaceutical pig 10, a person is advantageously protected from the threat of an unshielded needle because the syringe is contained within the sharps container.

Yet another advantage of the present invention is the prevention of the contamination of the radiopharmaceutical pig 10. During the transport of the syringe 14 to the hospital, the housing of the sharps container 12 advantageously prevents the inner cavity of the lower shield of the radiopharmaceutical pig from becoming contaminated. If the syringe leaks, the radioactive drug collects above the closed end 64 of the housing 26, thereby preventing the contamination of inner cavity of the lower shield 18. Furthermore, once the spent syringe is sealed within the sharps container, the inner cavities of the upper 16 and lower 18 shield are advantageously protected from contamination while the radiopharmaceutical pig is moved to the disposal area. Accordingly, the invention advantageously saves the expense of the cleaning of contaminated radiopharmaceutical pigs.

While a particular form of the invention has been illustrated and described, it will be apparent that various modifications can be made without departing from the spirit and scope of the invention. Accordingly, it is not intended that the invention be limited, except as by the appended claims.

I claim:

1. A transportation container for a syringe containing radioactive material comprising, a radiopharmaceutical pig having an interior surface defining an internal chamber, the radiopharmaceutical pig including radiation-resistant material surrounding the chamber; and a sharps container having a cap and a housing sized to fit within the chamber of the radiopharmaceutical pig,
   the cap and the housing each having a closed end and an open mating end, with one of the mating ends fitting inside the other to fixedly retain the cap to the housing in an assembled state, the assembled cap and housing having an interior surface sized to hold the syringe therein.

2. The transport container as defined in claim 1, wherein the housing has a window through which at least part of the syringe is visible when it is inside the fastened container.

3. The transport container as defined in claim 1, wherein the housing is constructed from a transparent material.

4. The transport container as defined in claim 1, wherein the mating end of the cap has at least two resilient snaps; and the mating end of the housing has at least two ledges, each of which is aligned with an associated resilient snap.

5. The transportation container as described in claim 1, wherein the mating end of the cap includes at least two radially spaced, cylindrical ridges extending longitudinally toward the mating end of the closure;

the mating end of the housing further including a cylindrical sealing wall extending longitudinally to fit between the ridges on the cap when the housing is attached to the cap, thereby creating a leak resistant seal.

6. The transportation container as defined in claim 1, wherein the mating end of the cap fits inside the mating end of the housing.

* * * * *